(12) United States Patent
Ji

(10) Patent No.: US 10,702,362 B2
(45) Date of Patent: Jul. 7, 2020

(54) BRACKET PACKAGING CARTRIDGE AND METHOD FOR CLAMPING BRACKET

(71) Applicant: GUANGZHOU OO MEDICAL SCIENTIFIC LIMITED, Guangzhou (CN)

(72) Inventor: Li Ji, Guangzhou (CN)

( * ) Notice: Subject to any disclaimer, the term of this patent is extended or adjusted under 35 U.S.C. 154(b) by 235 days.

(21) Appl. No.: 15/798,398

(22) Filed: Oct. 31, 2017

(65) Prior Publication Data
US 2018/0338823 A1 Nov. 29, 2018

(30) Foreign Application Priority Data
May 23, 2017 (CN) .......................... 2017 1 0369770

(51) Int. Cl.
*A61C 19/02* (2006.01)
*A61C 7/12* (2006.01)
(Continued)

(52) U.S. Cl.
CPC .............. *A61C 19/02* (2013.01); *A61C 7/146* (2013.01); *A61B 50/20* (2016.02); *A61C 7/14* (2013.01);
(Continued)

(58) Field of Classification Search
CPC ......... A61B 50/30; A61B 50/20; A61B 50/33; A61B 2050/0056; A61B 2050/3008;
(Continued)

(56) References Cited

U.S. PATENT DOCUMENTS 860,648 A * 7/1907 Feldman ................ B65D 43/24
  40/313
883,906 A * 4/1908 Swan ........................ A47F 3/00
  312/123
(Continued)

FOREIGN PATENT DOCUMENTS

CN    201287863 Y    8/2009
CN    201361133 Y    12/2009
(Continued)

OTHER PUBLICATIONS

CN First Office Action dated Jan. 31, 2018 in the corresponding CN application(application No. 201710369770.7).
(Continued)

*Primary Examiner* — Gideon R Weinerth
(74) *Attorney, Agent, or Firm* — Novoclaims Patent Services LLC; Mei Lin Wong

(57) ABSTRACT

The present disclosure discloses a bracket packaging cartridge and a method for clamping a bracket. The bracket packaging cartridge includes a cartridge body, an inner support and a cover body. A placement cavity is arranged on the cartridge body, the inner support is arranged in the placement cavity, and the inner support is provided with a plurality of bracket placement grooves. The bracket placement groove is used for placing the bracket. The cover body and the cartridge body match each other. The bracket placement groove includes a placement opening portion, a placement side portion and a placement bottom portion. The placement side portion is provided with a retaining protrusion, and the placement bottom portion of the bracket placement groove is inclined.

6 Claims, 8 Drawing Sheets

(51) Int. Cl.
*A61C 7/14* (2006.01)
*B65D 25/10* (2006.01)
*A61C 19/00* (2006.01)
*A61B 50/20* (2016.01)

(52) U.S. Cl.
CPC .......... *A61C 19/00* (2013.01); *A61C 2202/00* (2013.01); *B65D 25/10* (2013.01); *B65D 25/107* (2013.01)

(58) Field of Classification Search
CPC .... A61B 2050/0053; A61B 2050/0084; A61B 50/22; A61B 50/24; A61C 19/02; A61C 7/14; A61C 7/146; A61C 7/02; A61C 7/00; A61C 2202/00; A61C 3/04; A61C 8/0087; A61C 19/00; B25H 3/003; B25H 3/02; B25H 3/023; B65D 43/24; B65D 5/522; B65D 25/10; B65D 25/107; B65D 43/14; B65D 51/249; E05C 17/00; A61G 15/14; A61G 15/16
USPC ...................... 433/9, 77, 26, 49, 79
See application file for complete search history.

(56) References Cited

U.S. PATENT DOCUMENTS

| | | | | |
|---|---|---|---|---|
| 1,989,159 | A * | 1/1935 | Gross | A47F 7/03 206/45.23 |
| 2,200,404 | A * | 5/1940 | Vogt | A47F 7/03 206/45.23 |
| 4,244,632 | A * | 1/1981 | Molinari | A45C 9/00 190/109 |
| 5,221,202 | A * | 6/1993 | James | A61C 7/12 206/369 |
| 5,328,363 | A * | 7/1994 | Chester | A61C 7/12 206/63.5 |
| 5,348,154 | A * | 9/1994 | Jacobs | A61C 7/12 206/368 |
| 5,692,609 | A * | 12/1997 | Lin | A61C 19/02 206/368 |
| 5,692,896 | A * | 12/1997 | Pospisil | A61C 7/14 206/369 |
| 5,697,780 | A * | 12/1997 | Tuneberg | A61C 7/12 206/369 |
| 5,827,058 | A * | 10/1998 | Kelly | A61C 7/12 433/9 |
| 6,450,328 | B1 * | 9/2002 | Machacek | A61C 19/02 206/45.2 |
| 7,090,073 | B2 * | 8/2006 | Barnes | A61C 19/10 206/368 |
| 9,504,544 | B2 * | 11/2016 | Conley | A61C 7/14 |
| 2005/0016884 | A1 * | 1/2005 | Stout | A61C 7/12 206/369 |
| 2005/0133384 | A1 * | 6/2005 | Cinader | A61C 7/16 206/63.5 |
| 2005/0178685 | A1 * | 8/2005 | Corcoran | A61C 7/12 206/369 |
| 2006/0068351 | A1 * | 3/2006 | Castner | A61C 7/14 433/2 |
| 2006/0127834 | A1 * | 6/2006 | Szwajkowski | A61C 7/00 433/2 |
| 2007/0138042 | A1 * | 6/2007 | Wood | A61C 3/04 206/369 |
| 2008/0166682 | A1 * | 7/2008 | Bjorn | A61C 3/04 433/77 |
| 2009/0188815 | A1 * | 7/2009 | Ahlers | A61C 19/00 206/63.5 |
| 2012/0273371 | A1 * | 11/2012 | Bathen | A61C 19/02 206/63.5 |
| 2013/0126367 | A1 * | 5/2013 | Kyung | A61C 7/12 206/206 |
| 2014/0170592 | A1 * | 6/2014 | Johansson | A61C 3/04 433/77 |
| 2015/0118642 | A1 * | 4/2015 | Conley | A61C 7/14 433/77 |
| 2016/0095682 | A1 * | 4/2016 | Hirsch | A61C 19/02 206/210 |
| 2018/0177577 | A1 * | 6/2018 | Conley | A61C 7/14 |
| 2018/0214258 | A1 * | 8/2018 | Ruan | A61C 7/14 |
| 2018/0338823 | A1 * | 11/2018 | Ji | A61C 19/02 |
| 2018/0339821 | A1 * | 11/2018 | Ji | A61C 7/14 |
| 2019/0069980 | A1 * | 3/2019 | Kapec | A61C 19/02 |
| 2020/0078141 | A1 * | 3/2020 | Ji | A61C 7/287 |

FOREIGN PATENT DOCUMENTS

| | | |
|---|---|---|
| CN | 102711660 A | 10/2012 |
| CN | 202987714 U | 6/2013 |
| CN | 203283689 U | 11/2013 |
| CN | 203738341 U | 7/2014 |
| CN | 204521027 U | 8/2015 |
| CN | 206857261 U | 1/2018 |
| KR | 2020100004404 U | 4/2010 |
| KR | 1020150115692 A | 10/2015 |

OTHER PUBLICATIONS

CN Second Office Action in the corresponding CN application(appiication No. 201710369770.7).
CN First Search Report dated Mar. 22,2018 in the corresponding CN application(application No. 201710369770.7).

* cited by examiner

BRACKET PACKAGING CARTRIDGE AND METHOD FOR CLAMPING BRACKET

CROSS REFERENCE TO RELATED APPLICATIONS

The present application claims the priority of Chinese Patent Application No. 201710369770.7, filed May 23, 2017, the entire disclosures of which are incorporated herein by reference.

FIELD

The present disclosure relates to the field of tooth orthodontics bracket, and more particularly, to a bracket packaging cartridge and a method for clamping a bracket.

BACKGROUND

Bracket is a component in orthodontic techniques. An arch wire applies various types of orthodontic forces to the teeth via the bracket. The main role of the brackets is to secure the arch wire, so that the arch wire can work better, and transmit the orthodontic force, in order to control the three-dimensional movement of the tooth, and achieve the purpose of orthodontic treatment.

A bracket packaging cartridge is a cartridge for packaging brackets, which can guarantee the safety of products during delivery, and enhance the product grade.

The existing bracket packaging cartridge generally includes a cartridge body, a cover body and an inner support. The inner support is arranged inside the cartridge body, and provided with bracket placement grooves. The bracket placement grooves are used for placing the brackets. When an orthodontist performs an orthodontic treatment, the orthodontist needs to take the brackets out of the bracket placement grooves with a clamping tool. Since both of the teeth and brackets are tilted, the orthodontist needs to make a great adjustment to the clamping angle of the bracket after the bracket being taken out, and attach the bracket onto the tooth. However, the adjustment of the clamping angle of the bracket brings great inconvenience to the orthodontist to perform the orthodontic treatment, and also makes the orthodontic treatment more complicated and increases operation time. In addition, due to the great adjustment of the clamping angle of the bracket, the bracket may be fallen down or even lost at the time of operation. Further, since the positions of the brackets is not limited in the bracket packaging cartridge during transportation or moving, the brackets are easy to fall off, causing the brackets for different tooth positions confusion.

SUMMARY

An objective of the present disclosure is to provide a bracket packaging cartridge and a method for clamping a bracket, which may facilitate and simplify an orthodontic treatment when an orthodontist performs the orthodontic treatment.

Technical solutions are provided as below.

A bracket packaging cartridge is provided, including a cartridge body, an inner support and a cover body, wherein a placement cavity is arranged on the cartridge body, the inner support is arranged in the placement cavity, the inner support is provided with a plurality of bracket placement grooves, each bracket placement groove is adapted to place the bracket, and the cover body matches the cartridge body; and the bracket placement groove includes a placement opening portion, a placement side portion and a placement bottom portion, the placement side portion of the bracket placement groove includes a top edge and a bottom edge, the top edge of the placement side portion of the bracket placement groove is in contact with the placement opening portion of the bracket placement groove, the bottom edge of the placement side portion of the bracket placement groove is in contact with the placement bottom portion of the bracket placement groove.

Further, the placement side portion of the bracket placement groove includes a first placement side portion and a second placement side portion, the first placement side portion faces the second placement side portion;

the first placement side portion is provided with a first retaining protrusion at a bottom edge of the first placement side portion, the first retaining protrusion protrudes from the first placement side portion to the second placement side portion, and a retaining gap is provided between the first retaining protrusion and the placement bottom portion of the bracket placement groove; and the second placement side portion is provided with a second retaining protrusion at a bottom edge of the second placement side portion, the second retaining protrusion protrudes from the second placement side portion to the first placement side portion, and a retaining gap is provided between the second retaining protrusion and the placement bottom portion of the bracket placement groove, and the second retaining protrusion faces the first retaining protrusion.

Further, the first placement side portion is provided with a first side concave between the first retaining protrusion and the placement bottom portion of the bracket placement groove, and the first side concave is smoothly connected to the first retaining protrusion and the placement bottom portion of the bracket placement groove;

the second placement side portion is provided with a second side concave between the second retaining protrusion and the placement bottom portion of the bracket placement groove, and the second side concave is smoothly connected to the second retaining protrusion and the placement bottom portion of the bracket placement groove; and the first side concave and the second side concave both have an curved surface.

Further, the first placement side portion is provided with a first avoiding portion above the first retaining protrusion, the first avoiding portion is connected with the first retaining protrusion, and the first avoiding portion is avoided in a direction opposite to a protruding direction of the first retaining protrusion; and the second placement side portion is provided with a second avoiding portion above the second retaining protrusion, the second avoiding portion is connected with the second retaining protrusion, and the second avoiding portion is avoided in a direction of opposite to a protruding direction of the second retaining protrusion.

Further, the placement side portion of the bracket placement groove further includes a third placement side portion and a forth placement side portion opposite to the third placement side portion; and each of the third placement side portion and the forth placement side portion has a bottom edge, and a top edge gradually tilted in a direction towards the bottom edge, angles respective formed by the third placement side portion and the forth placement side portion with the placement bottom portion of the bracket placement groove enable a clamping tool entering the bracket placement groove smoothly.

Further, the third placement side portion and the forth placement side portion both have curved surfaces, each of the third placement side portion and the forth placement side portion has a curved top edge, each of the third placement side portion and the forth placement side portion has a straight or curved bottom edge, and the top edge of each of the third placement side portion and the forth placement side portion is gradually reduced toward the respective bottom edge.

Further, a plane of the placement opening portion of the bracket placement groove is parallel to the bottom support surface of the bracket packaging cartridge, and the placement bottom portion of the bracket placement groove is an inclined plane and is inclined relative to a bottom support surface of the bracket packaging cartridge.

Further, an end of the cover body is rotationally connected with an end of the cartridge body, the cover body is able to be turned relative to the cartridge body, and after turning the cover body, a bottom of the cover body is formed into a bottom support surface of the bracket packaging cartridge, the cover body is at an angle appropriate for clamping to the cartridge body, and the placement bottom portion of the bracket placement groove is at an angle appropriate for clamping to the bottom support surface of the bracket packaging cartridge.

Further, a fastening protrusion, a stop protrusion and a supporting component are arranged on at least one side of both sides of the cover body, a distance is left between the fastening protrusion and the stop protrusion, an end of the fastening protrusion is provided with a retaining protrusion, the supporting component is provided with a rotating hole and a stop groove, the supporting component is rotatablly connected with the fastening protrusion through the rotating hole, and the stop groove and the stop protrusion match each other; and a position protrusion is arranged on at least one side of both sides of the cartridge body, and the position protrusion corresponds to the stop protrusion, and matches the stop groove.

Further, the supporting component is further provided with a position groove, the position groove and the position protrusion match each other, the position groove is arranged between the rotating hole of the supporting component and the stop groove, and the position groove is orientated to a same or opposite orientation of the stop groove.

Further, the bottom support surface is absorbable or attachable to a working table.

Further, a lower surface of another end of the cartridge body is provided with a step; and when the bracket packaging cartridge is placed on the working table, a bottom support surface of the step is the bottom support surface of the bracket packaging cartridge, the another end of the cartridge body is inclined to one end of the cartridge body, the placement bottom portion of the bracket placement groove is inclined, and the placement bottom portion of the bracket placement groove is at an angle appropriate for clamping to the bottom support surface of the bracket packaging cartridge.

Further, the inner support is provided with at least one inclined portion, and a surface of the inclined portion is at an angle appropriate for clamping to the bottom support surface of the bracket packaging cartridge; and a plurality of bracket placement grooves are arranged on the inclined portion of the inner support, the placement bottom portion of the bracket placement groove is tilted, the placement bottom portion of the bracket placement groove is at an angle appropriate for clamping to the bottom support surface of the bracket packaging cartridge, and the placement bottom portion of the bracket placement groove is parallel to the inclined portion of the inner support.

Further, brackets are placed in the bracket placement grooves of the bracket packaging cartridge, the brackets placed in the bracket placement grooves are arranged in a same direction and a same occlusal direction as the brackets to be attached on the tooth surfaces.

A method for clamping a bracket is further provided, comprising:

placing a bracket in a bracket placement groove of a bracket packaging cartridge, wherein a bottom edge of the bracket is at an angle appropriate for clamping to a bottom support surface of the bracket packaging cartridge;

putting clamping ends of a clamping tool into the bracket placement groove of the bracket packaging cartridge, wherein during putting the clamping ends of a clamping tool into the bracket placement groove of the bracket packaging cartridge, a bottom edge of each clamping end of the clamping tool is at an angle appropriate for clamping to the bottom support surface of the bracket packaging cartridge;

extending the clamping ends of the clamping tool from a placement opening portion of the bracket placement groove to a placement bottom portion of the bracket placement groove along a placement side portion of the bracket placement groove, until the clamping ends of the clamping tool are extended to a clamping position of the bracket;

applying clamping force on the clamping tool, wherein the clamping ends of the clamping tool are located on both sides of the bracket, the bracket is clamped by the clamping ends of the clamping tool, and the bottom edge of each clamping end of the clamping tool is at an angle appropriate for clamping to the bottom support surface of the bracket packaging cartridge; and taking the bracket out of the bracket placement groove, after the bracket is clamped by the clamping ends of the clamping tool, wherein the bottom edge of each clamping end of the clamping tool is at an angle appropriate for clamping to the bottom edge of the bracket.

It should note the following instructions.

The above the terms "first" and "second" do not represent a specific number or order, and these terms may be used to distinguish one feature/element from another feature/element.

A mesial direction and a distal direction, the "mesial direction" may present a direction of the tooth closer to a mid-line of the face, and the "distal direction" may represent a direction of the tooth farther away from the mid-line of the face.

The above "occlusal direction" may present the occlusal direction of the teeth.

The advantages or principles of the present disclosure will be described below:

1. The bracket packaging cartridge includes a cartridge body, an inner support and a cover body. The inner support is arranged in the cartridge body, and the inner support is provided with a plurality of bracket placement grooves. Each bracket placement groove is adapted to place a bracket. The bracket placement groove has a placement opening portion, a placement side portion and a placement bottom portion. The placement bottom portion of the bracket placement groove is tilted, and the placement bottom portion of the bracket placement groove is at an angle appropriate for clamping to the bottom support surface of the bracket packaging cartridge. Because the placement bottom portion of the bracket placement groove is tilted, the whole of the bracket can be tilted when the bracket is placed in the bracket placement groove, and the bottom edge of the bracket is at an angle appropriate for clamping to the bottom support surface of the bracket packaging cartridge.

When the orthodontist performs an orthodontic treatment, the clamping ends of the clamping tool may be put into the bracket placement groove of the bracket packaging cartridge, and the clamping ends of the clamping tool may be extended from the placement opening portion of the bracket placement groove to the placement bottom portion of the bracket placement groove along the placement side portion of the bracket placement groove, until the clamping ends of the clamping tool are extended to the clamping position of the bracket. The orthodontist may apply clamping force on the clamping tool, so that the bracket is clamped by the clamping ends of the clamping tool. During clamping, the bottom edge of each clamping end of the clamping tool 1 is at an angle appropriate for clamping to the bottom support surface of the bracket packaging cartridge. Then the orthodontist may take the bracket out of the bracket placement groove in a form that the bottom edge of the clamping end of the clamping tool is at an angle appropriate for clamping to the bottom edge of the bracket.

For such bracket packaging cartridge, when clamping the bracket, the orthodontist may use a clamping tool to clamp and take out the bracket at an appropriate angle according to requirements. After the bracket is taken out, the orthodontist makes no adjustment to the clamping angle of the bracket to attach the bracket onto the tooth directly, or makes a slight adjustment if necessary. This brings great convenience to the orthodontic treatment, and simplifies the orthodontic treatment, to significantly reduce duration of operation, and increase efficiency of the orthodontic treatment. In addition, it can avoid influence on the orthodontic treatment caused by the falling or even lost of the bracket since the clamping angle of the bracket should be adjusted largely.

2. In the bracket placement groove, the first placement side portion faces the second placement side portion. The first placement side portion is provided with a first retaining protrusion at the bottom edge of the first placement side portion, and the second placement side portion is provided with a second latch portion at the bottom edge of the second placement side portion. The first retaining protrusion faces the second retaining protrusion. The first retaining protrusion and the second retaining protrusion are configured so that the bracket can be retained to avoid the movement of the bracket in the bracket placement groove, and avoid the bracket falling out from the bracket placement groove, when the bracket is placed in the bracket placement groove. It can effectively ensure the safety of the bracket in transit and improve the protection of the bracket.

3. The first placement side portion is provided with a first side concave between the first retaining protrusion and the placement bottom portion of the bracket placement groove. The second placement side portion is provided with a second side concave between the second retaining protrusion and the placement bottom portion of the bracket placement groove. The first side concave and the second side concave both have curved surfaces. The first side concave and the second recessed portion are configured so that it is convenient to remain the bracket in the bracket placement groove when putting the bracket into the bracket placement groove, and it is also convenient to take the bracket out of the bracket placement groove.

4. The first placement side portion is provided with a first avoiding portion above the first retaining protrusion, and a second placement side portion is provided with a second avoiding portion above the second retaining protrusion. The first avoiding portion and the second avoiding portion are configured to play an avoiding function during putting the bracket into the bracket placement groove or taking the bracket out of the bracket placement groove, which facilitates the bracket into and out of the bracket placement groove.

5. In the bracket placement groove, the third placement side portion faces the fourth placement side portion. The top edge of each of the third placement side portion and the fourth placement side portion is gradually inclined in the direction towards the bottom edge, and the angles formed by the third placement side portion and the placement bottom portion of the bracket placement groove, and formed by the forth placement side portion and the placement bottom portion of the bracket placement groove allow the clamping tool to smoothly enter the bracket placement groove. The third placement side portion and the fourth placement side portion are configured to facilitate the access of the bracket, especially bring great convenience for the orthodontist to clamp the bracket. It thus can effectively improve the efficiency of clamping the bracket.

6. The top edge of each of the third placement side portion and the fourth placement side portion is curved. The bottom edge of each of the third placement side portion and the fourth placement side portion is a straight line. The top edge of each of the third placement side portion and the fourth placement side portion is gradually reduced toward the bottom edge. The placement opening portion of the bracket placement groove becomes smaller toward the placement bottom portion of the bracket placement groove. Such configuration may play a supporting role to retain the bracket, while facilitating the bracket into and out of the bracket placement groove. It shows the rationality of the space design of the bracket placement groove.

7. The bottom surface of the cartridge body is the bottom support surface of the bracket packaging cartridge. The plane of the placement opening portion of the bracket placement groove is parallel to the bottom support surface of the bracket packaging cartridge. The placement bottom portion of the bracket placement groove is an inclined plane, and it is inclined relative to the plane of the placement opening portion of the bracket placement groove. The angle formed by the placement bottom portion of the bracket placement groove and the plane of the placement opening portion of the bracket placement groove is appropriate for clamping. When the bracket packaging cartridge is placed on the working table, the bracket placed in the bracket placement groove is inclined relative to the bottom support surface of the bracket packaging cartridge. The angle formed by the bottom edge of the bracket and the bottom support surface of the bracket packaging cartridge is an appropriate for clamping.

8. The cover body is rotatablly connected with the cartridge body, and the cover body can be turned to a certain angle with respect to the cartridge body. The angle formed by the overturned cover body and the cartridge body is appropriate for clamping. The bottom support surface of the cover body is the bottom support surface of the bracket packaging cartridge. The angle formed by the placing bottom of the bracket placement groove and the bottom support surface of the bracket packaging cartridge body is appropriate for clamping. After the turning the cover body of the bracket packaging cartridge, when the overturned bracket packaging cartridge is placed on the working table, the cover body is below the cartridge body, the bottom support surface is in contact with the working table, the cartridge body is tilted with respect to the cover body and the working table. The angle formed by the cartridge body and the bottom support surface of the cover body is appropriate for clamping. The angle formed by the placing bottom of the bracket placement groove and the bottom support surface of the bracket packaging cartridge is appropriate for clamping.

9. The cover body is provided with a fastening protrusion, a stop protrusion and a supporting component on a side of the cover body. A certain space is left between the fastening protrusion and the stop protrusion. The supporting component is provided with a rotating hole and a stop groove. The supporting component is rotatablly connected with the fastening protrusion. The stop groove and the stop protrusion match each other. A position protrusion is arranged on the side portion of the cartridge body. The position protrusion and the stop protrusion match each other. After turning the cover body of the bracket packaging cartridge, the position protrusion on the side portion of the cartridge body is engaged with the stop groove of the supporting component. The cartridge body is fastened, and the cartridge body and the cover body form an angle. When the bracket packaging cartridge is placed on the working table after the cover body of the bracket packaging cartridge has been turned, the cover body is below the cartridge body, the bottom support surface of the cover body is in contact with the working table, and the cartridge body is tilted in respect with the cover body and the working table. The angle formed by the cartridge body and the bottom support surface of the cover body is appropriate for clamping. The angle formed by the placement bottom portion of the bracket placement groove and the bottom support surface of the cover body is appropriate for clamping.

When the bracket packaging cartridge is closed, the stop groove of the supporting component may cooperate with the stop protrusion on the side portion of the cover body to fasten the supporting component.

10. The configuration of the position groove on the supporting component may be used to change the relative position between the cartridge body and the cover body, to adjust the angle formed by the cartridge body and the cover body.

11. The bottom support surface is absorbable or attachable onto the working table. When the overturned bracket packaging cartridge is placed on the working table, the bottom support surface can play a good skid resistant function. The bottom support surface is connected with the working table in a skid resistant form, thus there is a greater friction coefficient. During the usage, the friction force between the bottom support surface and the working table is great. The bracket packaging cartridge is difficult to move under a general force, it thus plays an anti-skid role.

12. The lower surface of another end of the cartridge body is provided with the step. When the bracket packaging cartridge is placed on the working table, the bottom support surface of the step is the bottom support surface of the bracket packaging cartridge, the another end of the cartridge body is inclined to one end of the cartridge body, the placement bottom portion of the bracket placement groove is inclined, and the placement bottom portion of the bracket placement groove is at an angle appropriate for clamping to the bottom support surface of the bracket packaging cartridge.

13. The inner support is provided with at least one inclined portion, and the surface of the inclined portion is at an angle appropriate for clamping to the bottom support surface of the bracket packaging cartridge. A plurality of bracket placement grooves are arranged on the inclined portion of the inner support, the placement bottom portion of the bracket placement groove is tilted, the placement bottom portion of the bracket placement groove is at an angle appropriate for clamping to the bottom support surface of the bracket packaging cartridge, and the placement bottom portion of the bracket placement groove is parallel to the inclined portion of the inner support. When the bracket packaging cartridge is placed on the working table, the angle formed by the placement bottom portion of the bracket placement groove and bottom support surface of the bracket packaging cartridge is appropriate for clamping.

14. The brackets placed in the bracket placement grooves are arranged in a same direction and a same occlusal direction as the brackets to be attached on the tooth surfaces. In this way, the orthodontist does not need to adjust the position of the bracket after taking the bracket out of the bracket placement groove. It can facilitate the orthodontist to accurately and quickly clamp the bracket and attach the bracket to a corresponding tooth.

DESCRIPTION OF THE REFERENCE SIGNS

10 denotes a cartridge body; 11 denotes a position protrusion; 12 denotes a inner support; 121 denotes a inclined portion; 13 denotes a bracket placement groove; 131 denotes a placement opening portion; 132 denotes a placement side portion; 1321 denotes a first placement side portion; 1321a denotes a first retaining protrusion; 1321b denotes a first side concave; 1321c denotes a first avoiding portion; 1322 denotes a second placement side portion; 1322a denotes a second retaining protrusion; 1322b denotes a second side concave; 1322c denotes a second avoiding portion; 1323 denotes a third placement side; 1324 denotes a fourth placement side; 133 denotes a placement bottom portion; 14 denotes a step; 20 denotes a cover body; 23 denotes a fastening protrusion; 231 denotes a retaining protrusion; 24 denotes a stop protrusion; 25 denotes a supporting component; 251 denotes a rotating hole; 252 denotes a stop groove; 253 denotes a position groove; and 30 denotes a bracket.

DETAILED DESCRIPTION OF THE EMBODIMENTS

Embodiments of the present disclosure will be described in detail below.

First Embodiment

Figure 1:
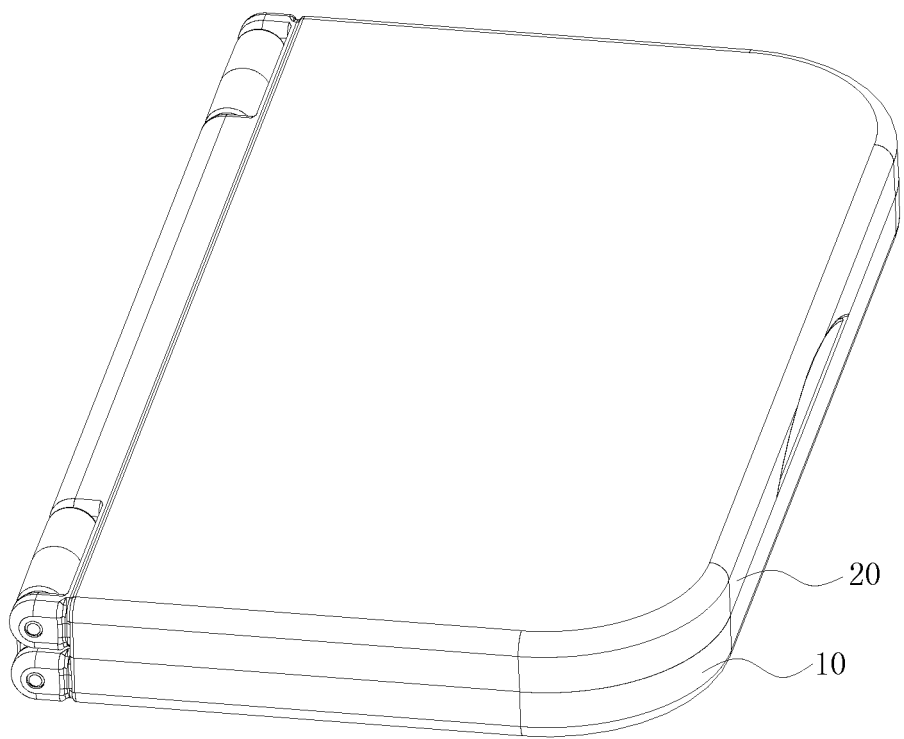
FIG. 1 is a schematic diagram illustrating a three-dimensional structure of a bracket packaging cartridge according to a first embodiment of the present disclosure in a close state.
Figure 2:
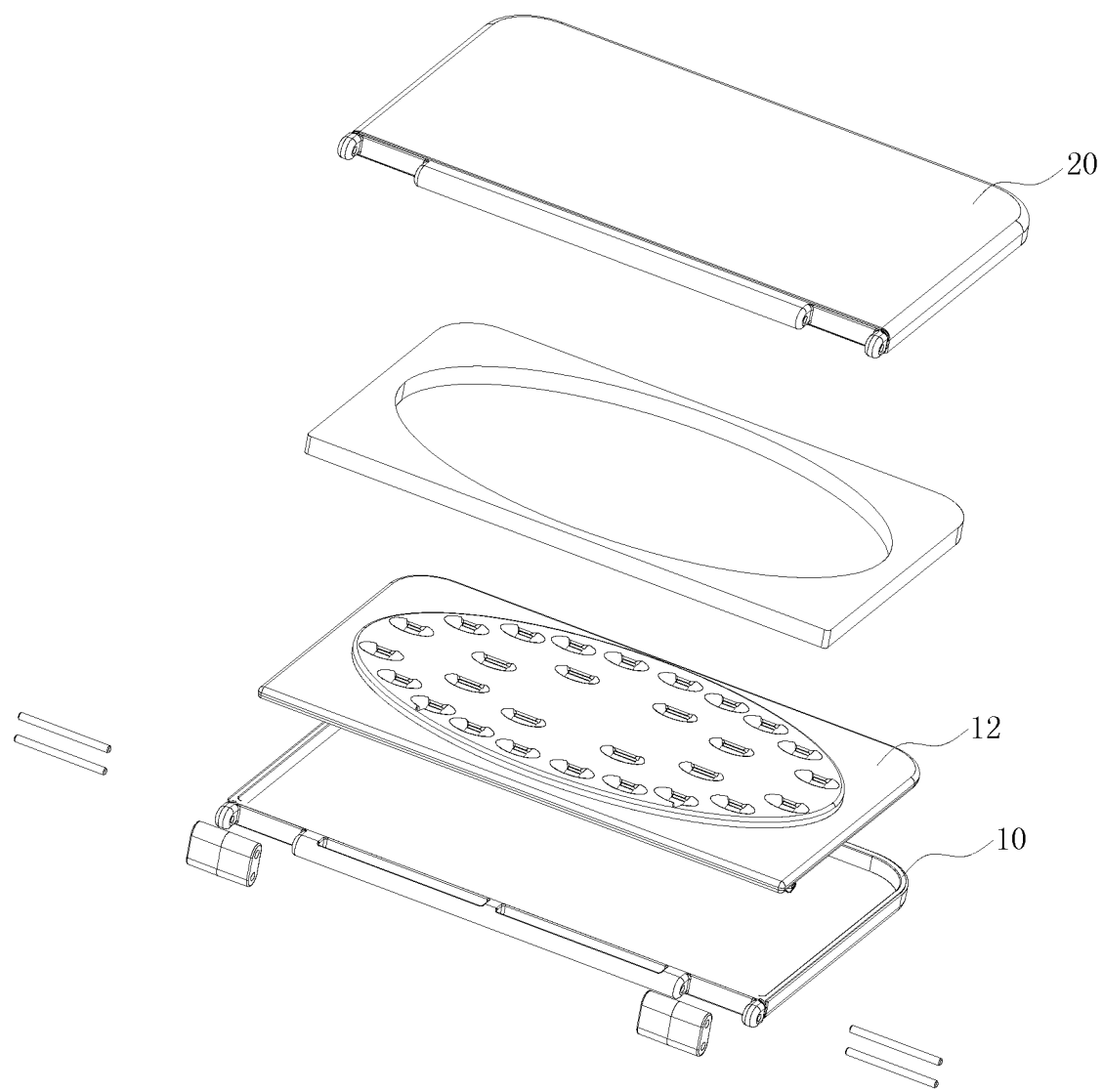
FIG. 2 is an exploded diagram of the bracket packaging cartridge according to the first embodiment of the present disclosure.
Figure 3:
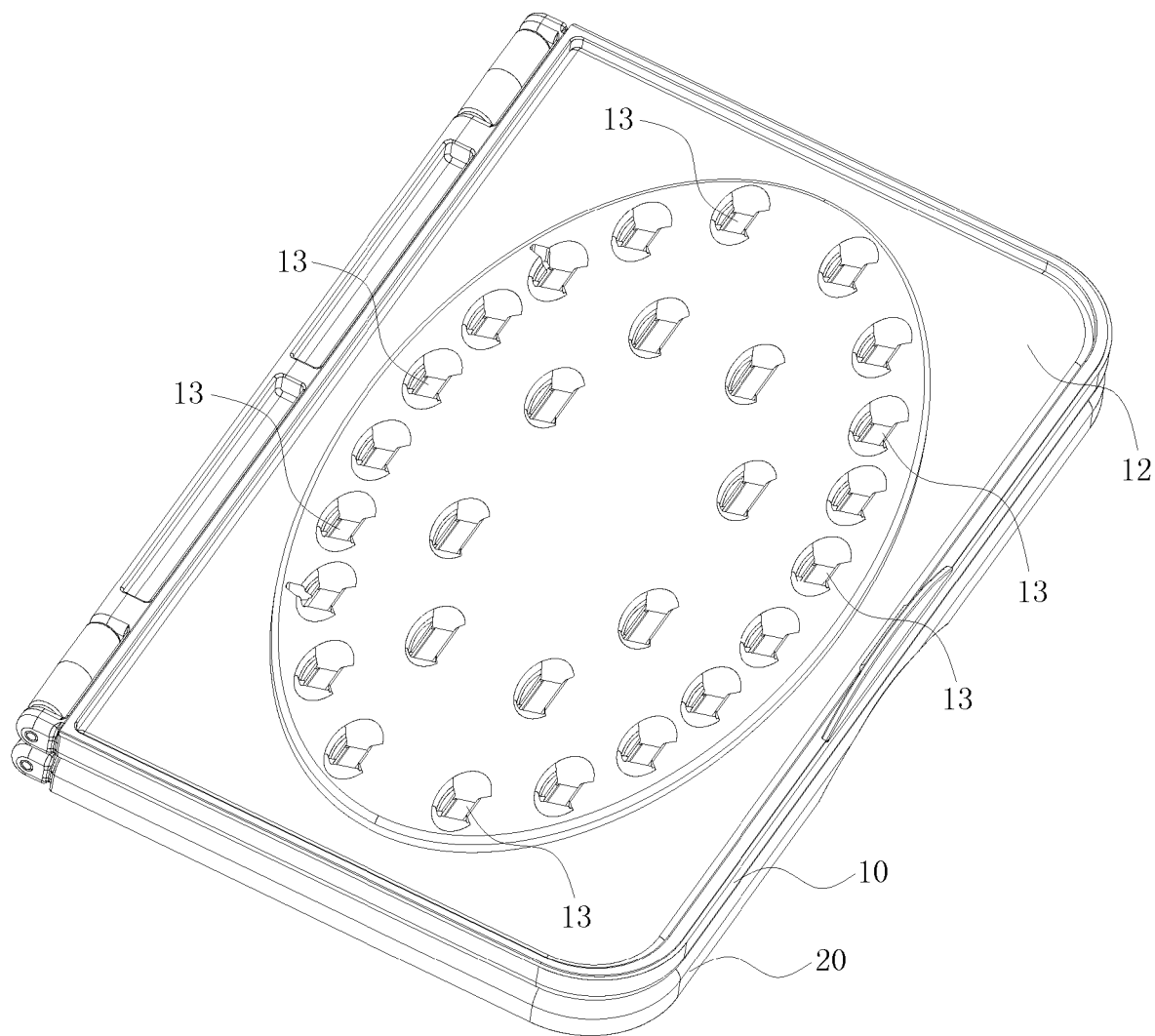
FIG. 3 is a schematic diagram illustrating a three-dimensional structure of the bracket packaging cartridge according to the first embodiment of the present disclosure in an open state.
Figure 4:
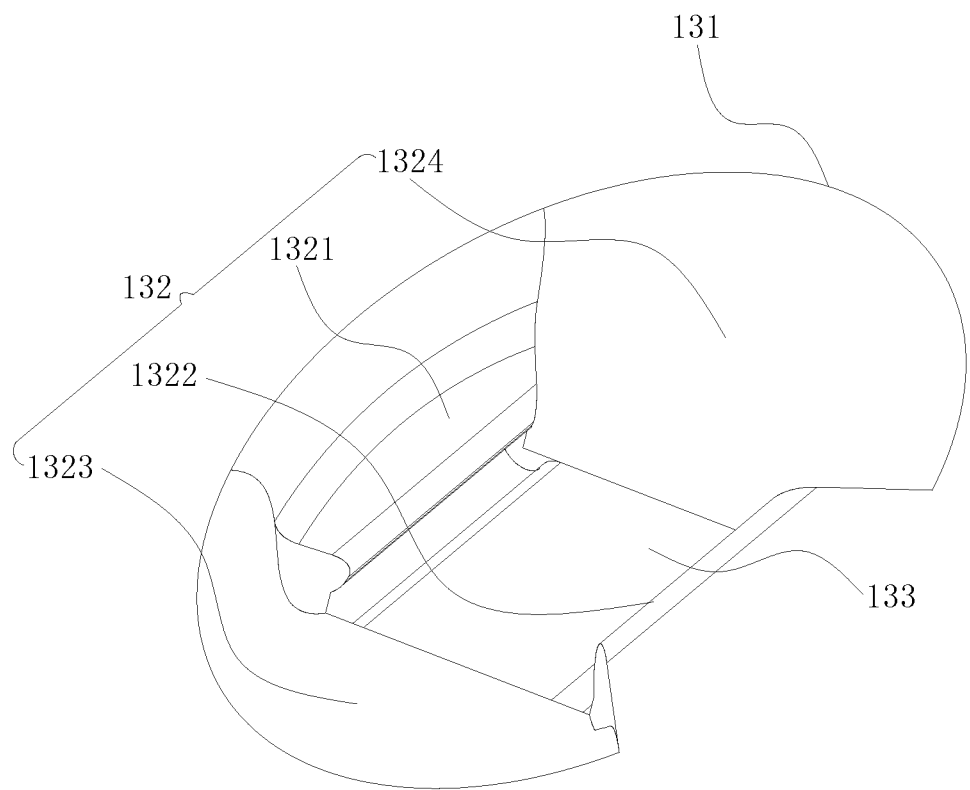
FIG. 4 is a schematic diagram illustrating a three-dimensional structure of a bracket placement groove according to the first embodiment of the present disclosure.
Figure 5:
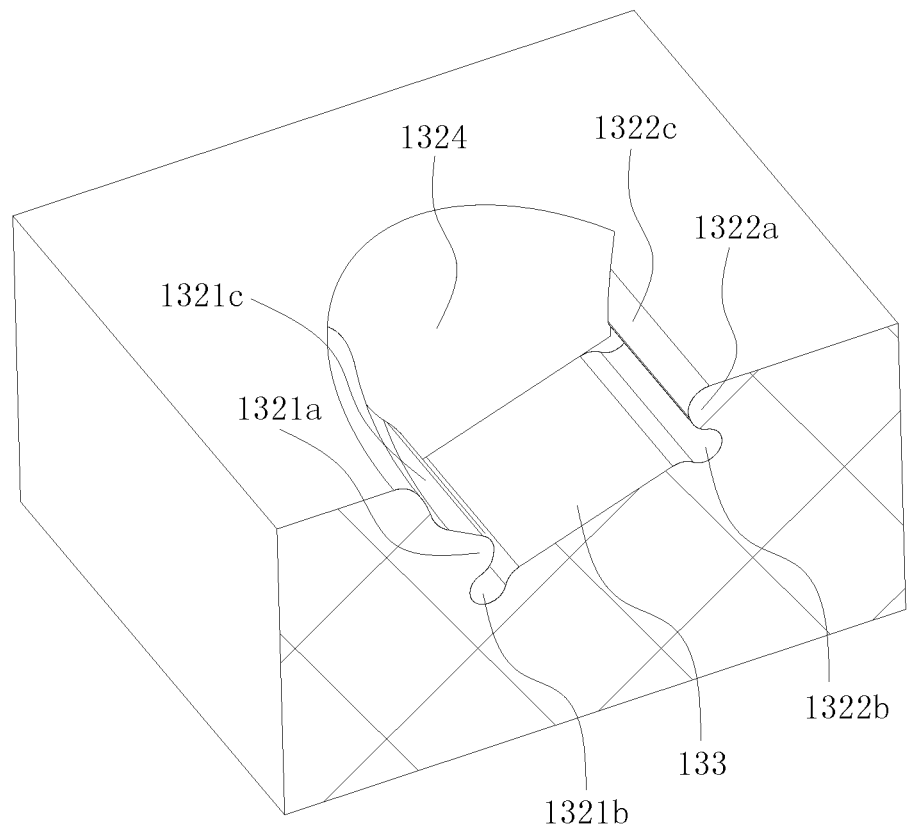
FIG. 5 is a schematic diagram illustrating a three-dimensional structure of a part of the bracket placement groove according to the first embodiment of the present disclosure.
Figure 6:
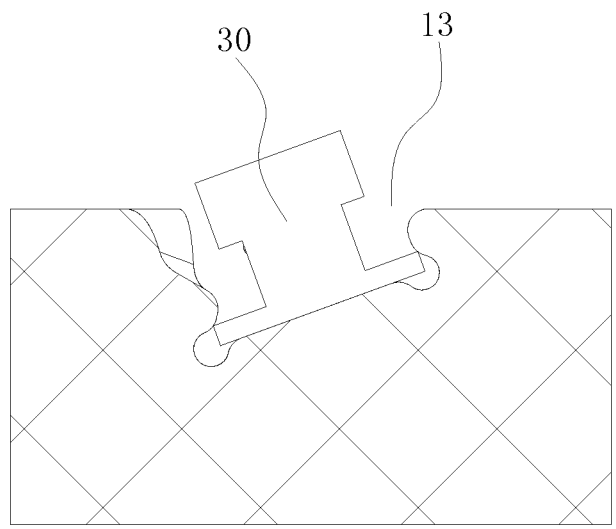
FIG. 6 is a schematic diagram illustrating a bracket placed on a bracket placement groove according to the first embodiment of the present disclosure.
Figure 7:
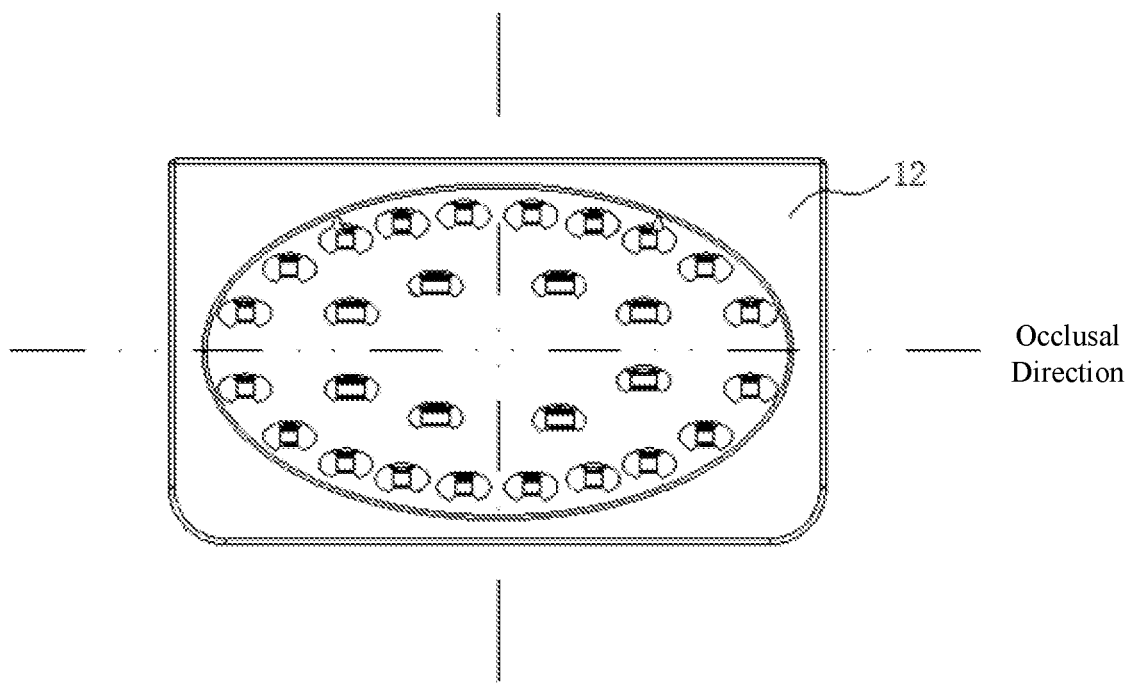
FIG. 7 is a schematic diagram illustrating a bracket placement groove in a direction and an occlusal direction according to the first embodiment of the present disclosure.
Figure 8:
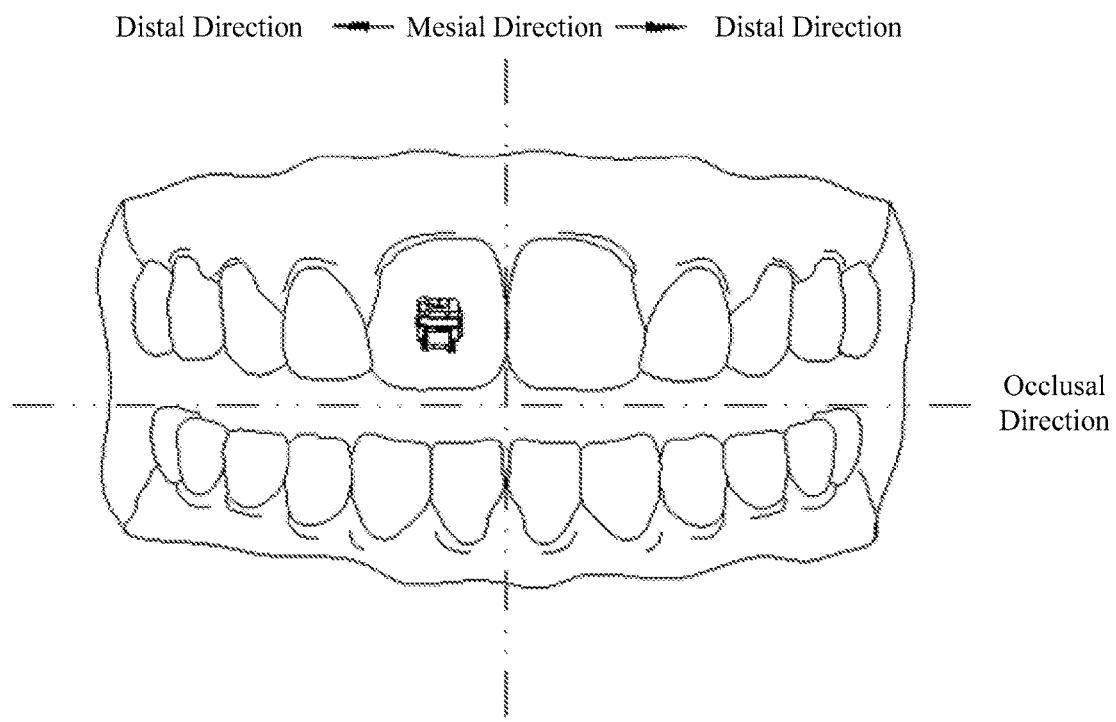
FIG. 8 is a schematic diagram illustrating teeth in the direction and the occlusion direction according to the first embodiment of the present disclosure.

As shown in FIGS. 1-8, a bracket packaging cartridge includes a cartridge body 10, an inner support 12 and a cover body 20. The cartridge body 10 is provided with a placement cavity, and the inner support 12 is arranged in the placement cavity of the cartridge body 10. The inner support is provided with a plurality of bracket placement grooves, each bracket placement groove 13 is adapted to place the bracket 30. The cover body and the cartridge body match each other, one end of the cover body 20 is rotatablly connected with one end of the cartridge body 10, and the cover body 20 is able to be turned relative to the cartridge body 10.

The bracket placement groove 13 includes a placement opening portion 131, a placement side portion 132 and a placement bottom portion 133. The placement side portion 132 of the bracket placement groove 13 includes a top edge and a bottom edge. The top edge of the placement side portion 132 of the bracket placement groove 13 is in contact with the placement opening portion 131 of the bracket placement groove.

The placement opening portion 131 of the bracket placement groove 13 extends along the placement side portion 132 of the bracket placement groove 13 to the placement bottom portion 133 of the bracket placement groove 13. The placement bottom portion 133 of the bracket placement groove 13 is inclined. The angle formed by the placement bottom portion 133 of the bracket placement groove 13 and the bottom support surface of the bracket packaging cartridge is appropriate for clamping, for example is between 0~90 degree.

In one embodiment, the angle formed by the placement bottom portion 133 of the bracket placement groove 13 and the bottom support surface of the bracket packaging cartridge is between 10~30 degrees. The angle formed by the placement bottom portion 133 of the bracket placement groove 13 and the bottom support surface of the bracket packaging cartridge depends on the different tooth positions.

In another embodiment, the angle formed by the placement bottom portion 133 of the bracket placement groove 13 and the bottom support surface of the bracket packaging cartridge is between 12~25 degrees. The angle formed by the placement bottom portion 133 of the bracket placement groove 13 and the bottom support surface of the bracket packaging cartridge depends on the different tooth position.

The plane of the placement opening portion 131 of the bracket placement groove 13 is parallel to the plane the bottom support surface of the bracket packaging cartridge. The plane of placement bottom portion 133 of the bracket placement groove 13 is a tilted plane, which is inclined with respect to the plane of the placement opening portion 131 of the bracket placement groove 13.

The placement side portion 132 of the bracket placement groove 13 includes a first placement side portion 1321 and a second placement side portion 1322. The first placement side portion 1321 faces the second placement side portion 1322.

The first placement side portion 1321 is provided with a first retaining protrusion 1321a at its bottom edge, the first retaining protrusion 1321a protrudes toward the second placement side portion 1322 relative to the first placement side portion 1321. A certain retaining gap is left between the first retaining protrusion 1321a and the placement bottom portion 133 of the bracket placement groove 13.

The second placement side portion 1322 is provided with a second retaining protrusion 1322a at its bottom edge. The second retaining protrusion 1322a protrudes toward the second placement side portion 1322 with respect to the first placement side portion 1321. A retaining gap is left between the second retaining protrusion 1322a and the placement bottom portion 133 of the bracket placement groove 13. The second retaining protrusion 1322a faces the first retaining protrusion 1321a.

The first placement side portion 1321 is provided with a first side concave 1321b between the first retaining protrusion 1321a and the placement bottom portion 133 of the bracket placement groove 13. The first side concave 1321b is smoothly connected to the first retaining protrusion 1321a and the placement bottom portion 133 of the bracket placement groove 13.

The second placement side portion 1322 is provided with a second side concave 1322b between the second retaining protrusion 1322a and the placement bottom portion 133 of the bracket placement groove 13. The second side concave 1322b is smoothly connected to the second retaining protrusion 1322a and the placement bottom portion 133 of the bracket placement groove 13.

The first side concave 1321b and the second side concave 1322b both have curved surfaces.

The first placement side portion 1321 is provided with a first avoiding portion 1321c above the first retaining protrusion 1321a. The first avoiding portion 1321c is connected with the first retaining protrusion 1321a. The first avoiding portion 1321c is avoided in a direction opposite to the protruding direction of the first retaining protrusion 1321a.

The second placement side portion 1322 is provided with a second avoiding portion 1322c above the second retaining protrusion 1322a. The second avoiding portion 1322c is connected with the second retaining protrusion 1322a. The second avoiding portion 1322c is avoided in a direction opposite to the protruding direction of the second retaining protrusion 1322a.

The placement side portion 132 of the bracket placement groove 13 also includes a third placement side portion 1323 and a forth placement side portion 1324, and the third placement side portion 1323 faces the forth placement side portion 1324.

The top edges of the third placement side portion 1323 and the forth placement side portion 1324 are gradually tilted to their bottom edges. The angles respective formed by the third placement side portion 1323 and the placement bottom portion 133 of the bracket placement groove 13, and the forth placement side portion 1324 and the placement bottom portion 133 of the bracket placement groove 13 are appropriate for the clamping tool to enter the bracket placement groove 13 smoothly, for example the angles are between 120~150 degrees respectively.

The third placement side portion 1323 and the forth placement side portion 1324 have curved surface. The top edges of the third placement side portion 1323 and the forth placement side portion 1324 are arc-shaped. The bottom edges of the third placement side portion 1323 and the forth placement side portion 1324 are straight or arc-shaped. In this embodiment, the bottom edge of the forth placement side portion 1324 is straight, the top edges of the third placement side portion 1323 and the forth placement side portion 1324 are gradually reduced toward their bottom edges.

The brackets are placed in the bracket placement grooves of the bracket packaging cartridge. The brackets placed in the bracket placement grooves are arranged in a same direction and a same occlusal direction as the brackets to be attached on the tooth surfaces.

A method for clamping a bracket includes the following steps:

placing a bracket 30 in a bracket placement groove 13 of a bracket packaging cartridge, wherein a bottom edge of the bracket 30 is at an angle appropriate for clamping, for example, at an angle between 0~90 degrees to a bottom support surface of the bracket packaging cartridge; putting clamping ends of a clamping tool into the bracket placement groove 13 of the bracket packaging cartridge, wherein during putting the clamping ends of a clamping tool into the bracket placement groove of the bracket packaging cartridge, a bottom edge of each clamping end of the clamping tool is at an angle appropriate for clamping, for example, at an angle between 0~90 degrees to the bottom support surface of the bracket packaging cartridge;

extending the clamping ends of the clamping tool from a placement opening portion 131 of the bracket placement groove 13 to a placement bottom portion 133 of the bracket placement groove 13 along a placement side portion 132 of the bracket placement groove 13, until the clamping ends of the clamping tool are extended to a clamping position of the bracket 30;

applying clamping force on the clamping tool, wherein the clamping ends of the clamping tool are located on both sides of the bracket 30, the bracket 30 is clamped by the clamping ends of the clamping tool, and the bottom edge of each clamping end of the clamping tool is at an angle appropriate for clamping, for example, at an angle between 0~90 degrees to the bottom support surface of the bracket packaging cartridge; and taking the bracket 30 out of the bracket placement groove, after the bracket 30 is clamped by the clamping ends of the clamping tool, wherein the bottom edge of each clamping end of the clamping tool is at an angle appropriate for clamping, for example, at an angle between 0~90 degrees to the bottom edge of the bracket 30.

The advantages of this embodiment are described as below.

1. The bracket packaging cartridge includes a cartridge body 10, an inner support 12 and a cover body 20. The inner support 12 is arranged in the cartridge body 10, the inner support 12 is provided with a plurality of bracket placement grooves 13, and each bracket placement groove 13 is adapted to place the bracket 30. The bracket placement groove 13 has a placement opening portion 131, a placement side portion 132 and a placement bottom portion 133. The placement bottom portion 133 of the bracket placement groove 13 is tilted, and the placement bottom portion 133 of the bracket placement groove 13 is at an angle appropriate for clamping (this angle is set according to the angle of the bracket tweezer itself and the use habit of the orthodontist, for example is between 0~90 degrees) the bottom support surface of the bracket packaging cartridge. Because the placement bottom portion 133 of the bracket placement groove 13 is tilted, the whole of the bracket 30 can be tilted when the bracket 30 is placed in the bracket placement groove 13, and the bottom edge of the bracket 30 is at an angle appropriate for clamping (this angle is set according to the angle of the bracket tweezer itself and the use habit of the orthodontist, for example is between 0~90 degrees) to the bottom support surface of the bracket packaging cartridge.

When the orthodontist performs an orthodontic treatment, the clamping ends may be put into the bracket placement groove 13 of the bracket packaging cartridge, and the clamping ends of the clamping tool may be extended from the placement opening portion 131 of the bracket placement groove 13 to the placement bottom portion 133 of the bracket placement groove 13 along the placement side portion 132 of the bracket placement groove 13, until the clamping ends of the clamping tool are extended to the clamping position of the bracket 30. The orthodontist may apply clamping force on the clamping tool, so that the bracket 30 is clamped by the clamping ends of the clamping tool. During clamping, the bottom edge of each clamping end of the clamping tool 1 is at an angle appropriate for clamping (this angle is set according to the angle of the bracket tweezer itself and the use habit of the orthodontist, for example is between 0~90 degrees) to the bottom support surface of the bracket packaging cartridge. Then the orthodontist may take the bracket 30 out of the bracket placement groove 13 in a form that the bottom edge of the clamping end of the clamping tool is at an angle appropriate for clamping to the bottom edge of the bracket 30.

For such bracket packaging cartridge, when clamping the bracket 30, the orthodontist may use a clamping tool to clamp and take out the bracket 30 at an appropriate angle according to requirements. After the bracket 30 is taken out, the orthodontist makes no adjustment to the clamping angle of the bracket 30 to attach the bracket onto the tooth directly, or makes a slight adjustment if necessary. This brings great convenience to the orthodontic treatment, and simplifies the orthodontic treatment, to significantly reduce duration of operation, and increase efficiency of the orthodontic treatment. In addition, it can avoid influence on the orthodontic treatment caused by the falling or even lost of the bracket 30 since the clamping angle of the bracket 30 should be adjusted largely.

2. In one embodiment, the angle formed by the placement bottom portion 133 of the bracket placement groove 13 and the bottom support surface of the bracket packaging cartridge is between 10~30 degree. The range of this angle is appropriate. The angle formed by the placement bottom portion 133 of the bracket placement groove 13 and the bottom support surface of the bracket packaging cartridge is depends on the different tooth positions.

3. In another embodiment, the angle formed by the placement bottom portion 133 of the bracket placement groove 13 and the bottom support surface of the bracket packaging cartridge is between 12~25 degree. The range of this angle is more appropriate. The angle formed by the placement bottom portion 133 of the bracket placement groove 13 and the bottom support surface of the bracket packaging cartridge is depends on the different tooth positions.

4. The bottom end surface of the cartridge body 10 is the bottom support surface of the bracket packaging cartridge. The plane of the placement opening portion 131 of the bracket placement groove 13 is parallel to the bottom support surface of the bracket packaging cartridge. The placement bottom portion 133 of the bracket placement groove 13 is a inclined plane, and it is inclined relative to the plane of the placement opening portion 131 of the bracket placement groove 13. The angle formed by the placement bottom portion 133 of the bracket placement groove 13 and the plane of the placement opening portion 131 of the bracket placement groove 13 is appropriate for clamping (this angle is set according to the angle of the bracket tweezer itself and the use habit of the orthodontist, for example is between 0~90 degrees). When the bracket packaging cartridge is placed on the working table, the bracket 30 placed in the bracket placement groove 13 is inclined relative to the bottom support surface of the bracket packaging cartridge. The angle formed by the bottom edge of the bracket 30 and the bottom support surface of the bracket packaging cartridge is appropriate for clamping (this angle is set according to the angle of the bracket tweezer itself and the use habit of the orthodontist, for example is between 0~90 degrees).

5. In the bracket placement groove 13, the first placement side portion 1321 faces the second placement side portion 1322. The first placement side portion 1321 is provided with a first retaining protrusion 1321a at its bottom edge, and the second placement side portion 1322 is provided with a second latch portion 1322a at its bottom edge, and the first retaining protrusion 1321a faces the second retaining protrusion 1322a. The first retaining protrusion 1321a and the second retaining protrusion 1322a are configured so that the bracket 30 can be retained to avoid the movement of the bracket 30 in the bracket placement groove 13, and avoid the bracket 30 falling out from the bracket placement groove 13, when the bracket 30 is placed in the bracket placement groove 13. It can effectively ensure the safety of the bracket in transit and improve the protection of the bracket 30.

6. The first placement side portion 1321 is provided with a first side concave 1321b between the first retaining protrusion 1321a and the placement bottom portion 133 of the bracket placement groove 13. The second placement side portion 1322 is provided with a second side concave 1322b between the second retaining protrusion 1322a and the placement bottom portion 133 of the bracket placement groove 13. The first side concave 1321b and the second side concave 1322b both have curved surfaces. The first side concave 1321b and the second recessed portion 1322b are configured so that it is convenient to remain the bracket 30 in the bracket placement groove 13 when putting the bracket 30 into the bracket placement groove 13, and it is also convenient to take the bracket 30 out of the bracket placement groove 13.

7. The first placement side portion 1321 is provided with a first avoiding portion 1321c above the first retaining protrusion 1321a, and a second placement side portion 1322 is provided with a second avoiding portion 1322c above the second retaining protrusion 1322a. The first avoiding portion 1321c and the second avoiding portion 1322c are configured to play an avoiding function during putting the bracket 30 into the bracket placement groove 13 or taking the bracket 30 out of the bracket placement groove 13, which facilitates the bracket 30 into and out of the bracket placement groove 13.

8. In the bracket placement groove 13, the third placement side portion 1323 faces the fourth placement side portion 1324. The top edges of the third placement side portion 1323 and the fourth placement side portion 1324 are gradually inclined along the direction to their bottom edges, and the angles formed by the third placement side portion 1323 and the placement bottom portion 133 of the bracket placement groove 13, and the fourth placement side portion 1324 and the placement bottom portion 133 of the bracket placement groove 13 allow the clamping tool to smoothly enter the bracket placement groove 13 (this angle is set according to the angle of the bracket tweezer itself and the use habit of the orthodontist, for example is between 120~150 degrees). The third placement side portion 1323 and the fourth placement side portion 1324 are configured to facilitate the access of the bracket 30, especially bring great convenience for the orthodontist to clamp the bracket 30. It thus can effectively improve the efficiency of clamping the bracket 30.

9. The top edges of the third placement side portion 1323 and the fourth placement side portion 1324 are curved. The bottom edges of the third placement side portion 1323 and the fourth placement side portion 1324 are straight line. The top edges of the third placement side portion 1323 and the fourth placement side portion 1324 gradually become smaller. The placement opening portion 131 of the bracket placement groove 13 becomes smaller toward the placement bottom portion 133 of the bracket placement groove 13. Such configuration may play a supporting role to retain the bracket 30, while facilitating the bracket 30 into and out of the bracket placement groove. It shows the rationality of the space design of the bracket placement groove 13.

10. The brackets placed in the bracket placement grooves are arranged in a same direction and a same occlusal direction as the brackets to be attached on the tooth surfaces. In this way, the orthodontist does not need to adjust the position of the bracket after taking the bracket out of the bracket placement groove. It can facilitate the orthodontist to accurately and quickly clamp the bracket and attach the bracket to a corresponding tooth.

Second Embodiment

Figure 9:
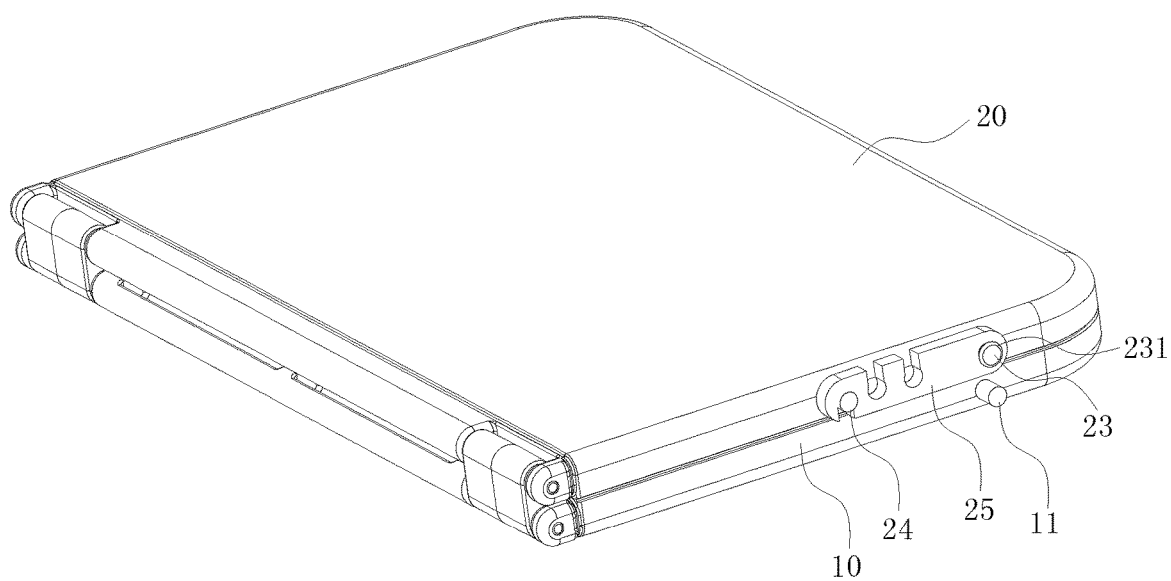
FIG. 9 is a schematic diagram illustrating a three-dimensional structure of a bracket packaging cartridge according to a second embodiment of the present disclosure in a close state.
Figure 10:
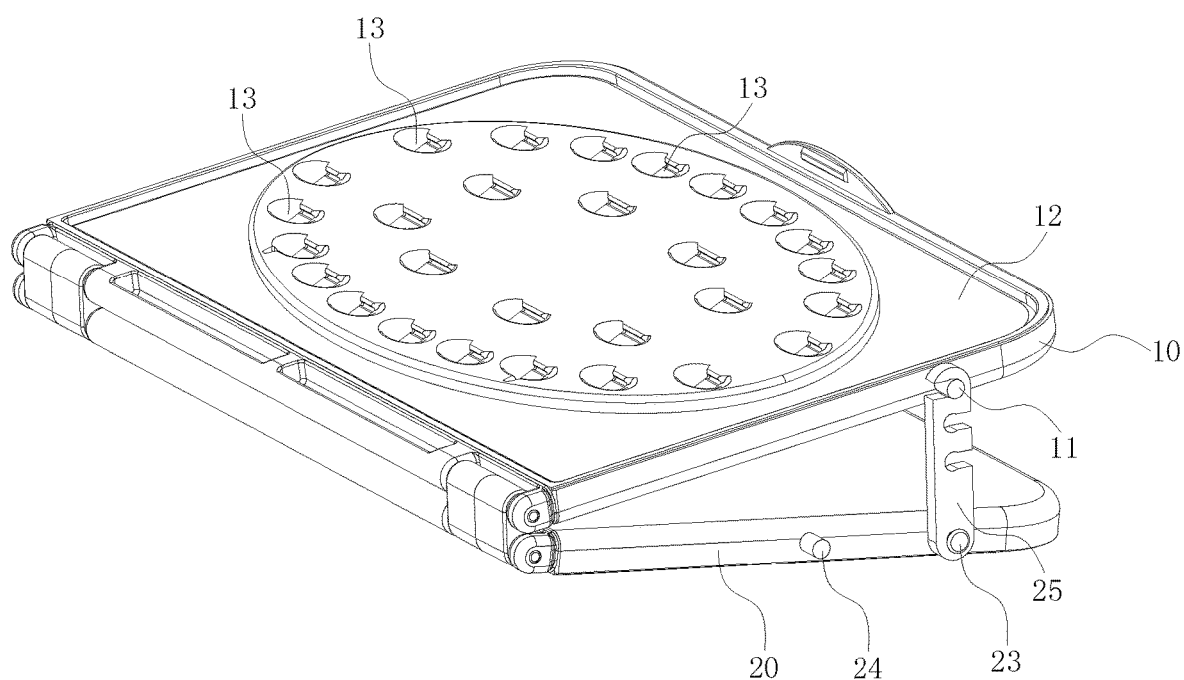
FIG. 10 is a schematic diagram illustrating a three-dimensional structure of the bracket packaging cartridge according to the second embodiment of the present disclosure after the bracket packaging cartridge has been turned.
Figure 11:
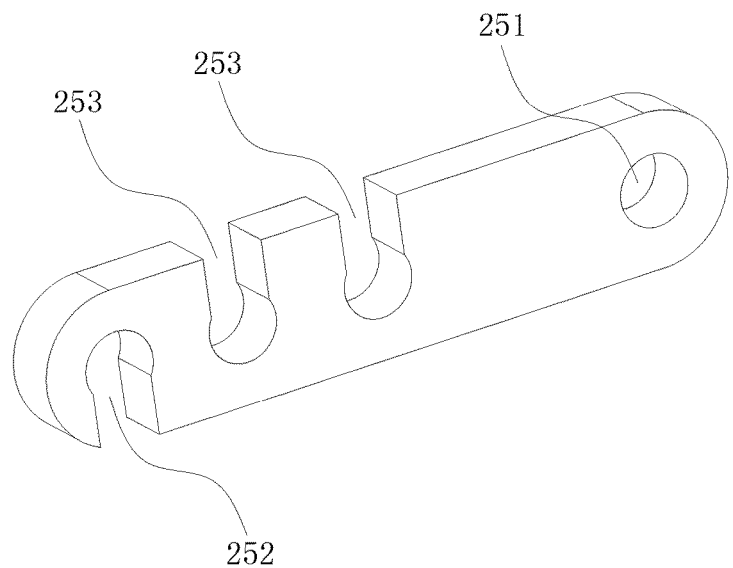
FIG. 11 is a schematic diagram illustrating a three-dimensional structure of a supporting component according to the second embodiment of the present disclosure.

As shown in FIGS. 1-6, 9 and 11, the differences between this embodiment and the first embodiment are described as below.

A fastening protrusion 23, a stop protrusion 24 and a supporting component 25 are arranged on at least one side of both sides of the cover body 20. A certain space is left between the fastening protrusion 23 and the stop protrusion 24. An end of the fastening protrusion 23 is provided with a retaining protrusion 231. The supporting component 25 is provided with a rotating hole 251 and a stop groove 252. The supporting component 25 is rotatablly connected with the fastening protrusion 23. The stop groove 252 and the stop protrusion 23 match each other.

A position protrusion 11 is arranged on at least one side of both sides of the cartridge body 10. The position protrusion 11 corresponds to the stop protrusion 24, and matches the stop groove 252.

The cover body 20 can be turned 360 degrees relative to the cartridge body 10. After the cover body 20 has been turned, the bottom of the cover body 20 is formed as the bottom support surface of the bracket packaging cartridge. The bottom support surface can be adsorbed or attached to the working table. The angle formed by the cover body 20 and the cartridge body 10 is appropriate for clamping, for example is between 0~90 degrees. The angle formed by the placement bottom portion 133 of the bracket placement groove 13 and the bottom support surface of the bracket packaging cartridge is appropriate for clamping, for example is between 0~90 degrees.

The support member 25 is further provided with a position groove 253. The position groove 253 matches the position protrusion 11. The position groove 253 is arranged between the rotating hole 251 of the supporting component 25 and the stop groove 252. The position groove 253 is orientated to a same or opposite orientation of the stop groove 252.

The advantages of this embodiment are described as below.

The cover body 20 is provided with a fastening protrusion 23, a stop protrusion 24 and a supporting component 25 on a side of the cover body 20. A certain space is left between the fastening protrusion 23 and the stop protrusion 24. The support member 25 is provided with a rotating hole 251 and a stop groove 252. The supporting component 25 is rotatablly connected with the fastening protrusion 23. The stop groove 252 and the stop protrusion 24 match each other. A position protrusion 11 is arranged on the side portion of the cartridge body 10. The position protrusion 11 and the stop protrusion 24 match each other. After turning the cover body 20 of the bracket packaging cartridge, the position protrusion 11 on the side portion of the cartridge body 10 is engaged with the stop groove 252 of the supporting component 25. The cartridge body 10 is fastened, and an angle is formed by the cartridge body 10 and the cover body 20. When the bracket packaging cartridge is placed on the working table after the cover body 20 of the bracket packaging cartridge has been turned, the cover body 20 is below the cartridge body 10, the bottom support surface of the cover body 20 is in contact with the working table, and the cartridge body 10 is tilted in respect with the cover body 20 and the working table. The angle formed by the cartridge body 10 and the bottom support surface of the cover body is appropriate for clamping. (this angle is set according to the angle of the bracket tweezer itself and the use habit of the orthodontist, for example is between 0~90 degrees). The angle formed by the placement bottom portion 133 of the bracket placement groove 13 and the bottom support surface of the cover body is appropriate for clamping (this angle is set according to the angle of the bracket tweezer itself and the use habit of the orthodontist, for example is between 0~90 degrees).

When the bracket packaging cartridge is closed, the stop groove 252 of the supporting component 25 may cooperate with the stop protrusion 24 on the side portion of the cover body 20 to fasten the supporting component 25.

The configuration of position groove 253 on the supporting component 25 may used to change the relative position between the cartridge body 10 and the cover body 20, to adjust the angle formed by the cartridge body 10 and the cover body 20.

The bottom support surface is absorbable or attachable onto the working table. When the overturned bracket packaging cartridge is placed on the working table, the bottom support surface can play a good skid resistant function. The bottom support surface is connected with the working table in a skid resistant form, thus there is a greater friction coefficient. During the usage, the friction force between the bottom support surface and the working table is great. The bracket packaging cartridge is difficult to move under a general force, it thus plays an anti-skid role.

Other configuration of this embodiment can be referred to the first embodiment, and will not be repeated herein.

Third Embodiment

Figure 12:
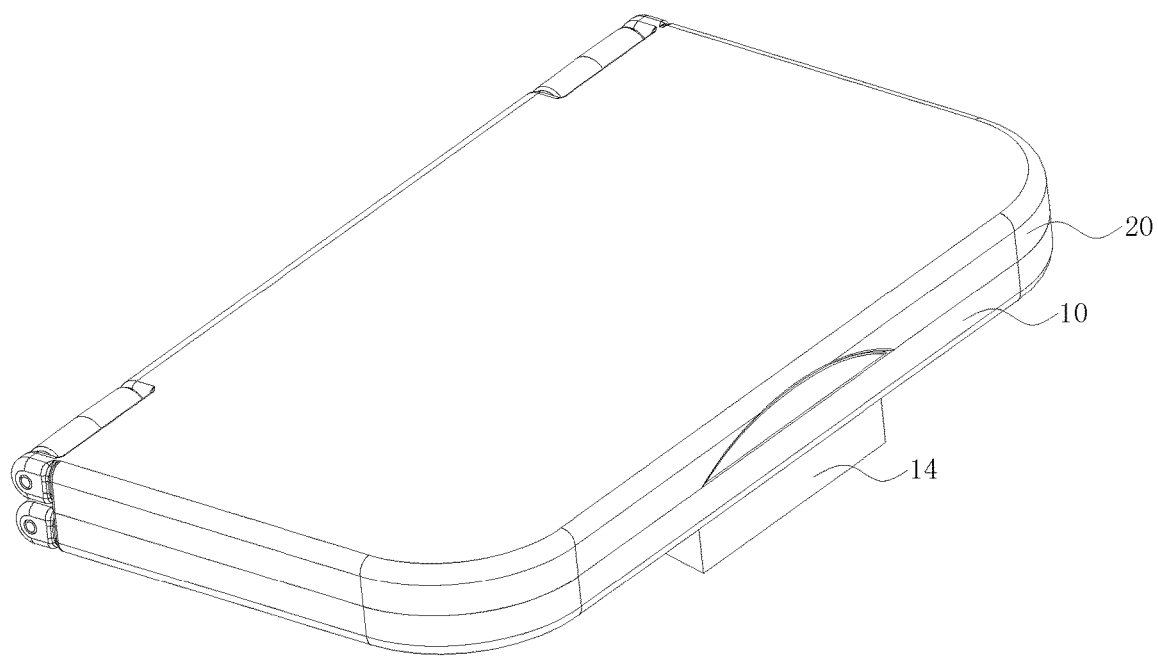
FIG. 12 is a schematic diagram of a three-dimensional structure of a bracket packaging cartridge according to a third embodiment of the present disclosure in a close state.

As shown in FIGS. 1-6 and 12, the differences between this embodiment and the first embodiment are described as below.

The lower surface of another end of the cartridge body 10 is provided with a step 14. When the bracket packaging cartridge is placed on the working table, the bottom support surface of the step 14 is the bottom support surface of the bracket packaging cartridge. The other end of the cartridge body 10 is tilted to one end of the cartridge body 10. The placement bottom portion 133 of the bracket placement groove 13 is inclined. The angle formed by the placement bottom portion 133 of the bracket placement groove 13 and the bottom support surface of the bracket packaging cartridge is appropriate for clamping, for example is between 0~90 degrees.

The advantages of this embodiment are described as below.

The lower surface of another end of the cartridge body 10 is provided with a step 14. When the bracket packaging cartridge is placed on the working table, the bottom support surface of the step 14 is the bottom support surface of the bracket packaging cartridge. The another end of the cartridge body 10 is tilted towards to one end of the cartridge body 10. The placement bottom portion 133 of the bracket placement groove 13 is inclined. The angle formed by the placement bottom portion 133 of the bracket placement groove 13 and the bottom support surface of the bracket packaging cartridge is appropriate for clamping (this angle is set according to the angle of the bracket tweezer itself and the use habit of the orthodontist, for example is between 0~90 degrees).

Other configuration of this embodiment can be referred to the first embodiment, and will not be repeated herein.

Fourth Embodiment

Figure 13:
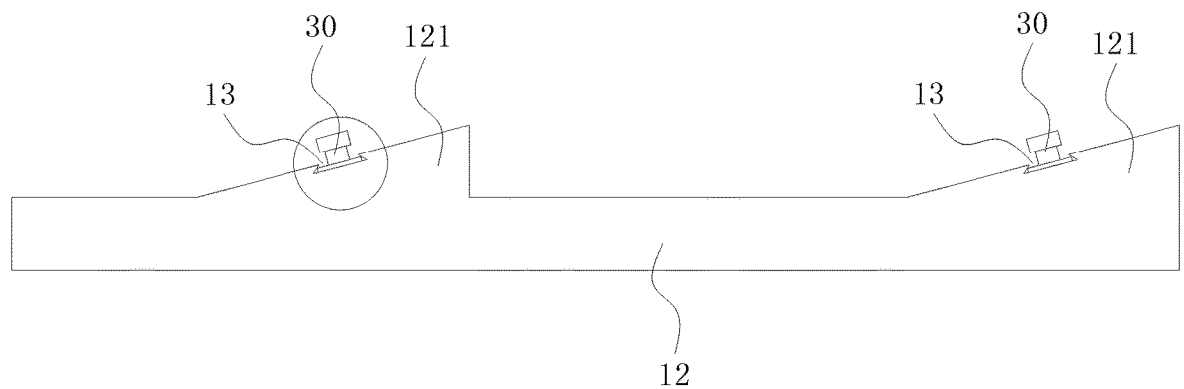
FIG. 13 is a side view of an inner support according to a fourth embodiment of the present disclosure.
Figure 14:
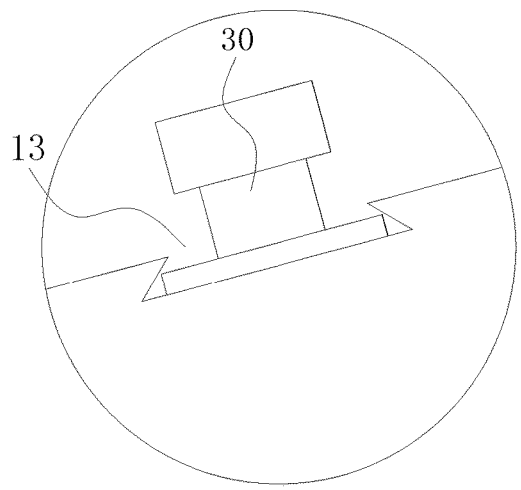
FIG. 14 is a partial enlarged view of FIG. 13.

As shown in FIGS. 1-FIGS. 6, 13 and 14, the differences between this embodiment and the first embodiment are described as below.

The inner support 12 is provided by at least one inclined portion 121. The angle formed by the surface of the inclined portion 121 and bottom support surface of the bracket packaging cartridge body is appropriate for clamping, for example is between 0~90 degrees. A plurality of bracket placement grooves 13 are arranged on the inclined portion 121 of the inner support 12. The placement bottom portion 133 of the bracket placement groove 13 is tilted. The angle formed by the placement bottom portion 133 of the bracket placement groove 13 and the bottom support surface of the bracket packaging cartridge is appropriate for clamping, for example is between 0~90 degrees, and the placement bottom portion 133 of the bracket placement groove 13 is parallel to the inclined portion 121 of the inner support 12.

The advantages of this embodiment are described as below.

The inner support 12 is provided with an inclined portion 121. The angle formed by the surface of the inclined portion 121 and bottom support surface of the bracket packaging cartridge body is appropriate for clamping, for example is between 0~90 degrees. A plurality of bracket placement grooves 13 is arranged on the inclined portion 121 of the inner support 12. The placement bottom portion 133 of the bracket placement groove 13 is tilted. The angle formed by the placement bottom portion 133 of the bracket placement groove 13 and the bottom support surface of the bracket packaging cartridge is appropriate for clamping (this angle is set according to the angle of the bracket tweezer itself and the use habit of the orthodontist, for example is between 0~90 degrees), and the placement bottom portion 133 of the bracket placement groove 13 is parallel to the inclined portion 121 of the inner support 12. When the bracket packaging cartridge is placed on the working table, the angle formed by the placement bottom portion 133 of the bracket placement groove 13 and bottom support surface of the bracket packaging cartridge is for clamping (this angle is set according to the angle of the bracket tweezer itself and the use habit of the orthodontist, for example is between 0~90 degrees).

Other configuration of this embodiment can be referred to the first embodiment, and will not be repeated herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A bracket packaging cartridge, comprising: a cartridge body, an inner support and a cover body,
   wherein a placement cavity is arranged on the cartridge body, the inner support is arranged in the placement cavity, the inner support is provided with a plurality of bracket placement grooves, each bracket placement groove is adapted to place a bracket; and
   the bracket placement groove includes a placement opening portion, a placement side portion and a placement bottom portion, the placement side portion of the bracket placement groove includes a top edge and a bottom edge, the top edge of the placement side portion of the bracket placement groove is in contact with the placement opening portion of the bracket placement groove, and the bottom edge of the placement side portion of the bracket placement groove is in contact with the placement bottom portion of the bracket placement groove,
   wherein the placement side portion of the bracket placement groove includes a first placement side portion and a second placement side portion, the first placement side portion faces the second placement side portion;
   the first placement side portion is provided with a first retaining protrusion at a bottom edge of the first placement side portion, the first retaining protrusion protrudes from the first placement side portion towards the second placement side portion, and a retaining gap is provided between the first retaining protrusion and the placement bottom portion of the bracket placement groove; and
   the second placement side portion is provided with a second retaining protrusion at a bottom edge of the second placement side portion, the second retaining protrusion protrudes from the second placement side portion towards the first placement side portion, and a retaining gap is provided between the second retaining protrusion and the placement bottom portion of the bracket placement groove, and the second retaining protrusion faces the first retaining protrusion,
   wherein the placement side portion of the bracket placement groove further includes a third placement side portion and a fourth placement side portion opposite to the third placement side portion; and
   each of the third placement side portion and the fourth placement side portion has a bottom edge, and a top edge gradually tilted in a direction towards the bottom edge, angles are respectively formed by the third placement side portion and the fourth placement side portion with the placement bottom portion of the bracket placement groove so as to enable a clamping tool entering the bracket placement groove smoothly.

2. The bracket packaging cartridge of claim 1, wherein the third placement side portion and the fourth placement side portion both have curved surfaces, each of the third placement side portion and the fourth placement side portion has a curved top edge, each of the third placement side portion and the fourth placement side portion has a straight or curved bottom edge, and a dimension of the top edge of each of the third placement side portion and the fourth placement side portion is greater than a dimension of the respective bottom edge so that the third placement side portion and the fourth placement side portion are tapered from the top edge towards the bottom edge respectively.

3. A bracket packaging cartridge, comprising: a cartridge body, an inner support and a cover body,
   wherein a placement cavity is arranged on the cartridge body, the inner support is arranged in the placement cavity, the inner support is provided with a plurality of bracket placement grooves, each bracket placement groove is adapted to place a bracket; and
   the bracket placement groove includes a placement opening portion, a placement side portion and a placement bottom portion, the placement side portion of the bracket placement groove includes a top edge and a bottom edge, the top edge of the placement side portion of the bracket placement groove is in contact with the placement opening portion of the bracket placement groove, and the bottom edge of the placement side portion of the bracket placement groove is in contact with the placement bottom portion of the bracket placement groove,
   wherein a plane of the placement opening portion of the bracket placement groove is parallel to the bottom support surface of the bracket packaging cartridge, and the placement bottom portion of the bracket placement groove is an inclined plane and is inclined relative to a bottom support surface of the bracket packaging cartridge.

4. A bracket packaging cartridge, comprising: a cartridge body, an inner support and a cover body,
   wherein a placement cavity is arranged on the cartridge body, the inner support is arranged in the placement cavity, the inner support is provided with a plurality of bracket placement grooves, each bracket placement groove is adapted to place a bracket; and
   the bracket placement groove includes a placement opening portion, a placement side portion and a placement bottom portion, the placement side portion of the bracket placement groove includes a top edge and a bottom edge, the top edge of the placement side portion of the bracket placement groove is in contact with the placement opening portion of the bracket placement groove, and the bottom edge of the placement side portion of the bracket placement groove is in contact with the placement bottom portion of the bracket placement groove, wherein an end of the cover body is rotationally connected with an end of the cartridge body, the cover body is turnable relative to the cartridge body, and after turning the cover body, a bottom of the cover body is formed into a bottom support surface of the bracket packaging cartridge, the cover body is at an angle appropriate for clamping to the cartridge body, and the placement bottom portion of the bracket placement groove is at an angle appropriate for clamping to the bottom support surface of the bracket packaging cartridge.

5. The bracket packaging cartridge of claim 4, wherein a fastening protrusion, a stop protrusion and a supporting component are arranged on at least one side of both sides of the cover body, a distance is left between the fastening protrusion and the stop protrusion, an end of the fastening protrusion is provided with a retaining protrusion, the supporting component is provided with a rotating hole and a stop groove, the supporting component is rotatably connected with the fastening protrusion through the rotating hole, and the stop groove and the stop protrusion match each other; and a position protrusion is arranged on at least one side of both sides of the cartridge body, and the position protrusion has a shape identical to the stop protrusion, and is complement to the stop groove in such a manner that the position protrusion is capable of engaging with the stop groove to lift the cartridge body and to secure the cartridge body in a tilted position.

6. The bracket packaging cartridge of claim 5, wherein the supporting component is further provided with a position groove, the position groove and the position protrusion match each other, the position groove is arranged between the rotating hole of the supporting component and the stop groove, and the position groove is orientated to a same or opposite orientation of the stop groove.

* * * * *